United States Patent [19]

Wang et al.

[11] Patent Number: 5,128,103
[45] Date of Patent: Jul. 7, 1992

[54] APPARATUS FOR AUTOMATICALLY PROCESSING MAGNETIC SOLID PHASE REAGENTS

[75] Inventors: Chi-Chin Wang, Wilmington, Del.; Robert T. McKeever, Landenberg; Marshall L. Salyers, Malvern, both of Pa.

[73] Assignee: E. I. Du Pont de Nemours and Company, Wilmington, Del.

[21] Appl. No.: 629,661

[22] Filed: Dec. 14, 1990

[51] Int. Cl.$^5$ .................. G01N 21/00; G01N 33/553; B03C 1/30; C12M 1/40
[52] U.S. Cl. .......................... 422/64; 435/287; 435/288; 436/526; 436/177; 422/681; 422/82.05; 210/222; 209/223.1
[58] Field of Search ............... 422/64, 67, 68.1, 82.05; 436/177, 526, 47, 49; 209/223.1; 210/222; 435/287, 803, 288

[56] References Cited

U.S. PATENT DOCUMENTS

| | | | |
|---|---|---|---|
| 3,933,997 | 1/1976 | Hersh et al. | 424/1 |
| 4,141,687 | 2/1979 | Forrest et al. | 210/222 |
| 4,234,538 | 11/1980 | Ginsberg et al. | 422/64 |
| 4,628,037 | 12/1986 | Chagnon et al. | 436/526 |
| 4,649,116 | 3/1987 | Daty et al. | 435/287 |
| 4,661,408 | 4/1987 | Lau et al. | 428/405 |
| 4,672,040 | 6/1987 | Josephson | 436/526 |
| 4,698,302 | 10/1987 | Whitehead et al. | 435/94 |
| 4,710,472 | 12/1987 | Saur et al. | 435/287 |
| 4,738,773 | 4/1988 | Müller-Ruchholtz et al. | 209/214 |
| 4,774,055 | 9/1988 | Wakatake et al. | 422/64 |
| 4,793,973 | 12/1988 | Ringrose | 422/102 |
| 4,863,693 | 9/1989 | Howell | 422/64 |
| 4,871,683 | 10/1989 | Harris et al. | 436/531 |
| 4,895,650 | 1/1990 | Wang | 210/222 |
| 4,988,618 | 1/1991 | Li et al. | 435/6 |

OTHER PUBLICATIONS

Advanced Magnetics Inc., "Magnetic Affinity Chromatography Starter Kit M4001 and Magnetic Affinity Chromatography Support Biomag M4100", Jul. 1984.

Primary Examiner—Robert J. Warden
Assistant Examiner—T. A. Trembley

[57] ABSTRACT

An automatic chemistry system having a wheel for mounting reaction vessels is provided with a programmable permanent magnet which is selectively positioned adjacent a reaction vessel to separate magnetizable particles in the vessel from the vessels liquid contents. This facilitates performing heterogeneous immunoassays.

5 Claims, 4 Drawing Sheets

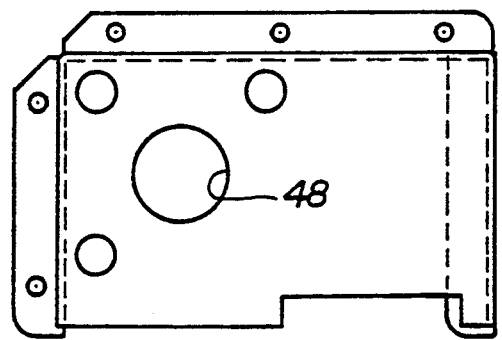
Fig. 6
Fig. 7
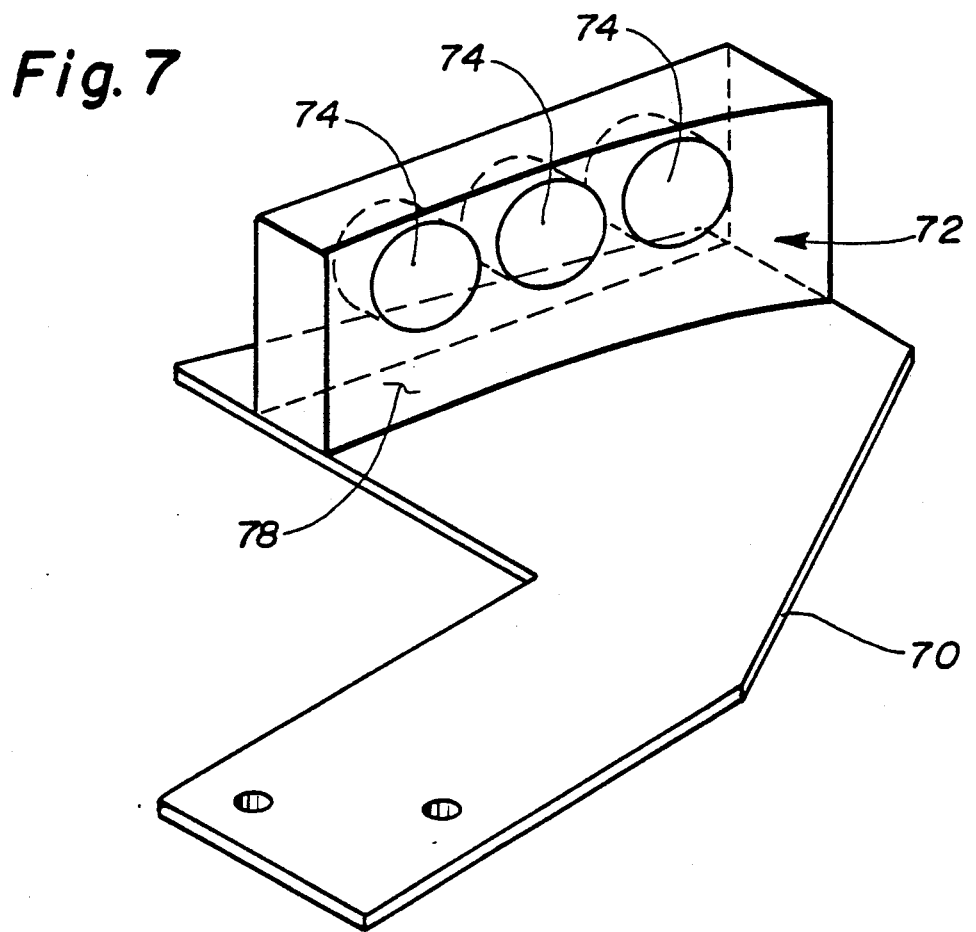

APPARATUS FOR AUTOMATICALLY PROCESSING MAGNETIC SOLID PHASE REAGENTS

CROSS REFERENCE TO RELATED APPLICATION

This invention relates to an application entitled Method and Apparatus for Automatically Processing Magnetic Solid Phase Reagents, Ser. No. 07/230,449, filed Aug. 10, 1988 (IP-0754).

FIELD OF THE INVENTION

The present invention relates to an automated apparatus for the separation and concentration of materials in small amounts of complex liquid mixtures

BACKGROUND OF THE INVENTION

Separation, isolation and concentration are process steps common to a chemical analysis. Often these steps are taken to remove interfering substances so that a subsequent chemical analysis can be performed. This "separation" stage can be performed several ways including solvent extraction, solvent evaporation and resin exchange. Magnetic separation, another technique for removing interfering substances, is a process of separation, isolation and concentration where the sought-for substance is attached or bound to magnetic particles. The magnetic particles offer advantages of handling including speed, convenience and low energy input. It is particularly suited to handling small samples. Advanced Magnetics Inc. of Cambridge, Mass. has been very active in this field in the application of their super paramagnetic particles to separation techniques. Their usage and properties is described in a product bulletin entitled Magnetic Affinity Chromatography Starter Kit M4001 and Magnetic Affinity Chromatography Support Biomag TM M4100 dated July 1984.

Magnetic particles are particularly useful in heterogeneous immunoassays as a solid support. To be useful as a solid support, the particles must be derivatized to permit the attachment of bioactive protein. Hersh et al. in their U.S. Pat. No. 3,933,997 describe the use of magnetically responsive particles for this purpose and use functionalized silanes as the intermediate between the particles and the bioactive protein.

There are essentially two types of heterogeneous immunoassays. These are competitive immunoassays and sandwich immunoassays. In a competitive assay, an antibody to an antigen contained in a first reagent is attached to the derivatized magnetic particles to make up a solid phase. The second reagent, consisting of antigen attached to a tag (a measurable entity, including radioactive molecules, fluorescent molecules, or enzymes), and patient sample are mixed with the solid phase in a test tube. In the absence of patient antigen, some 50% of the antigen-tag is bound to the antibody of the magnetic solid phase. In the presence of patient antigen, some of the antibodies are filled up with patient antigen and are unavailable to the tag antigen. As a result increasing amounts of patient antigen leads to decreasing amount of tag antigen. Thus one can form a calibration chart relating the amount of patient antigen to the amount of tag. The separation stage results from the need to measure the free tag or the bound tag, not the total tag added. The magnetic particle facilitates this separation by forming the particles with the bound tag into a pellet on the side of the tube. The free tag can then be removed as by aspiration. Following the separation and removal of free tag, another reagent is added so that the amount of bound tag can be measured. In a typical case, enzyme is used as the tag so that the reagent added is a "substrate" for the enzyme permitting the measurement of the amount of tag that was bound to antibody.

In a typical sandwich immunoassay, an antibody to an antigen is attached to the magnetic particle. This is in high concentration relative to the amount of patient antigen in a sample. Patient antigen is captured by the antibody on the magnetic particles and then the particles (and captured patient antigen) separated from interfering substances in the sample. To this, a second reagent, containing a second antibody with an attached tag, is added. This second antibody attaches to the patient antigen, captured by the first antibody on the magnetic particle, and results in the formation of a sandwich so that the second antibody tag is held firmly by the antigen to the first antibody on the magnetic particle. At this point, a magnetic separation similar to that described, permits the determination of bound tag which is in proportion to the patient antigen, the excess tag of the second reagent having been removed by aspiration.

Magnetic particles are particularly useful as the solid support in heterogeneous immunoassays because they can readily separate the free from the bound tag. Such immunoassays using magnetic particles as a solid support are described for example in U.S. Pat. No. 4,661,408 (Lau et al.), U.S. Pat. No. 4,628,037 issued to Chagnon et al., U.S. Pat. No. 4,672,040 issued to Josephson, and U.S. Pat. No. 4,698,302 issued to Whitehead et al. The methods disclosed in all of these patents relate to manual processes which utilize manual magnetic separation units such as those that are available from Corning Medical, Corning Glass Works, Medfield, Mass. Such manual techniques are relative slow, require relatively strong magnets which are expensive, require considerable manual dexterity, and require an excessive amount of time to effect the separation with the purity required, particularly for sandwich type heterogeneous immunoassay.

Technicon Corporation has offered an automated heterogeneous magnetic immunoassay system for some years. In this system the reagents are combined in a continuous flow process. Having reacted the reagents together, the process then brings the stream through a magnetic field where the magnetic particles are captured and, bound tag measured. The problem with this process is that of continuous flow systems in general. Carryover from one sample to the next tends to produce erroneous results, which error is reduced by reducing the number of samples analyzed per hour.

The Du Pont patented ACMIA technology for digoxin (DGN Method) has been used on the aca ® Discrete Analyzer using resin based column header as solid separation media. This assay has been adapted to run on the Dimension ® Clinical Chemistry System using chromium dioxide magnetic particles as the solid support. Unfortunately for both analyzers, manual treatment of the samples with antibody conjugate reagent (ABC) is required. The Dimension ® assay also involves treatment with chromium dioxide particle reagent (CPR), magnetic separation and transferring of the supernatant to the instrument for photometric measurement. This manual step required is not only time consuming but, because of the manual feature, is subject to error.

SUMMARY OF THE INVENTION

Many of these problems of the prior art assay and other analysis systems particularly those prior art systems using magnetic particles, i.e., particles that are responsive to a magnetic field, are reduced using the apparatus of this invention. The invention is particularly useful for those systems using robotic arms operating in conjunction with an assay wheel as a transport means for the reaction vessels or cuvettes. This invention permits magnetic particles to be used as a separable solid support in various analytical techniques and in automated fashion. This is particularly true and useful for heterogeneous assays which require that the solid support be removed and/or washed during the assay process.

According to this invention an automatic apparatus is provided for separating particles from aqueous particle dispersions disposed in a plurality of reaction vessels, the particle being responsive to a magnetic field, comprising: a transport means for moving the vessels in sequence past at least one processing position, a robotic arm for selectively processing the vessels as they move sequentially, and means for selectively subjecting the vessels to a magnetic field as they move sequentially, thereby to separate the particles from the aqueous dispersion.

In the preferred embodiment of the invention, the transport means indexes the vessels stepwise past the processing position and the reaction vessels each have walls and a longitudinal axis that is generally vertically disposed while the subjecting means field is generally transverse to the reaction vessel's longitudinal axis, whereby the particles are drawn toward a wall of the vessel. The subjecting means comprises a permanent magnetic which is positioned relative to the cuvette to have the flux axis of the magnet intersect the bottom center region of the cuvette. Preferably, the subjecting means is positioned on the robotic arm itself such that wherever the arm is positioned, proper cuvettes are automatically addressed.

In accordance with a further preferred embodiment of the invention, the subjecting means subjects a reaction vessel located either ahead or behind (indexing wise) the position of the robotic arm relative to a reaction vessel to a magnetic field. In another embodiment, the subjecting means simultaneously subjects three sequentially positioned reaction vessel to the magnetic field, such that a vessel containing a magnetizable dispersion can index through and be subjected to the magnetic field up to three times.

The invention also includes an automatic apparatus for use in assays for separating magnetic particles from a liquid phase, the apparatus comprising: a plurality of reaction vessels adapted to hold magnetic particles dispersed in a liquid phase, a reaction vessel mounting wheel adapted to move the reaction vessels in sequence past at least one processing position, probe means for dispensing liquid into and withdrawing liquid from the vessels, a reaction monitoring arm capable of relative movement with respect to the wheel and being positioned with its periphery adjacent any of the reaction vessels, a detector positioned on the arm radially outside the reaction vessels, the monitoring arm being operable to direct a beam of interrogating radiation through each vessel to the detector, and coupling means coupled to the arm for positioning a first magnet adjacent the location of the beam of interrogating radiation, but spaced therefrom by the distance separating adjacent reaction vessels on the wheel.

The apparatus of this invention eliminates the need for pretreatment of assays involving a magnetic solid support. It permits all necessary reagents to be delivered directly to a reaction vessel to perform the necessary incubations, separate the magnetic particles (CPR) from the solution, withdrawing the reacted material from the reaction vessel, and transferring it to a second reaction vessel for photometric measurement. This invention greatly facilitates the automation of the assay since the magnet module is controlled by the software used in controlling the automatic clinical chemistry system itself. It facilitates the performance of many heterogeneous assays on automatic clinical chemistry systems such as the Affinity Chromatography Media Immunoassay (ACMIA) using magnetic chromium dioxide particles as a solid support. Although this assay does not require washing, the apparatus of this invention also permits the clinical chemistry system to wash the solid support where necessary.

BRIEF DESCRIPTION OF THE DRAWINGS

The invention will be better understood with reference to the several drawings, in which like reference numerals are used to indicate like components, in which:

FIG. 6 is a front elevation view of the cover of the photodetector to which the magnet of FIGS. 4 and 5 is attached; and FIG. 7 is a pictorial view of an alternative embodiment of this invention for attaching three magnets to the reaction monitoring arm.

DESCRIPTION OF THE PREFERRED EMBODIMENT

Figure 1:
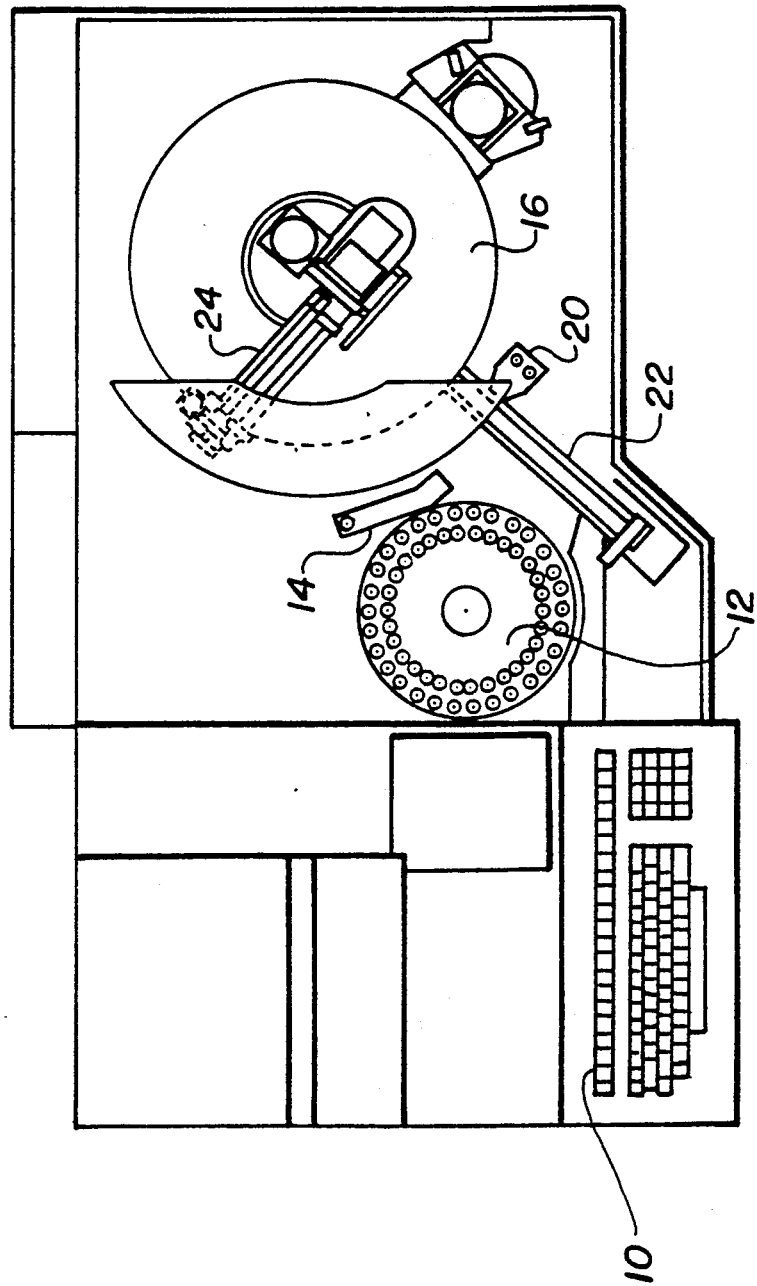
FIG. 1 is a pictorial plan view of an automatic clinical chemistry system in which this invention may find use.

There is illustrated in FIG. 1 an automated clinical chemistry system with which this invention finds use. This particular clinical chemistry system is an analyzer known as the Dimension ® clinical chemistry system sold by E. I. du Pont de Nemours and Company, Wilmington, Del. The system includes a computer 10 with appropriate display and keyboard. It also includes a sample carousel or wheel 12 together with a sample arm 14 and probe (not shown) for transferring samples to a cuvette or reaction vessel 17 (FIG. 2) on a cuvette wheel or transport means 16.

Figure 2:
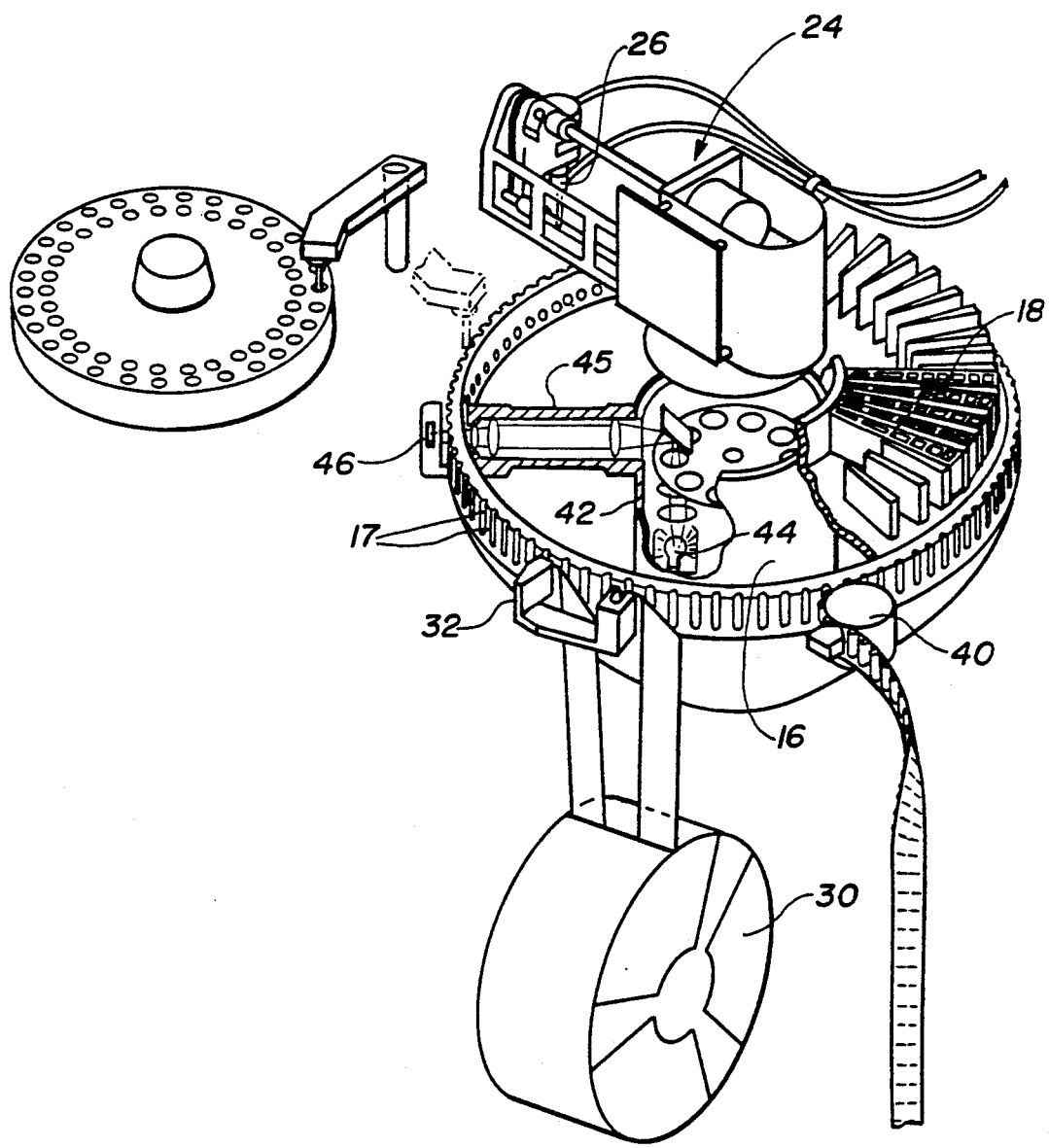
FIG. 2 is a pictorial representation of the sample wheel and arm assemblies, the reagent arm and probe, and transport means of the clinical analyzer system of FIG. 1.
Figure 3:
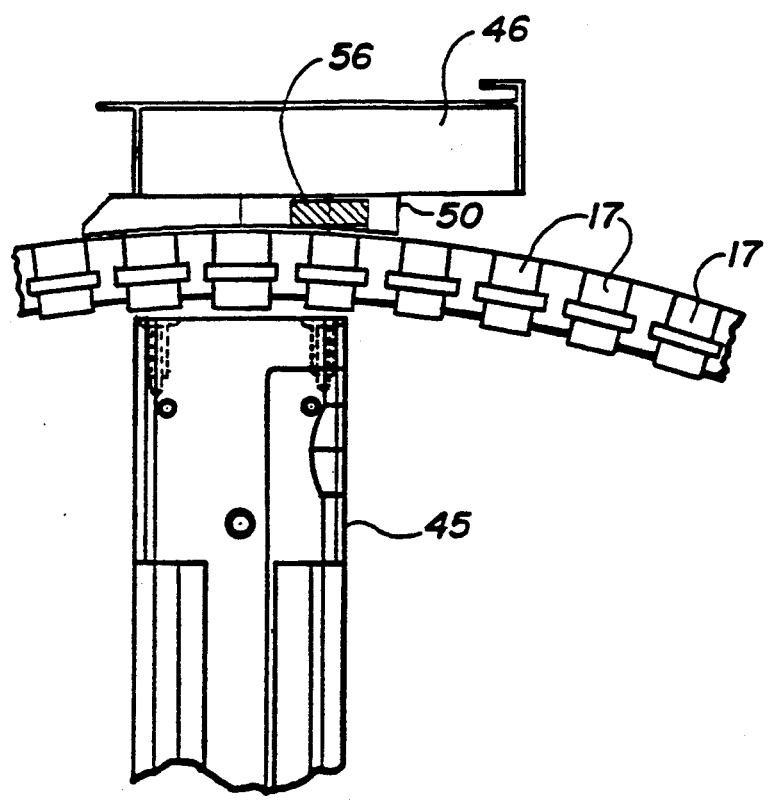
FIG. 3 is a fragmentary plan view of the reaction monitoring arm of FIG. 2 incorporating a magnet of this invention to effect removal of the CPR from reaction vessels.

The Dimension ® clinical chemistry system uses a Flex TM reagent cartridge 18 (FIG. 2). The cartridge contains a bar code which is read by a bar code reader 20 (FIG. 1) as the cartridges are introduced onto the transport means 16 via a reagent shuttle 22. A reagent arm 24 and probe 26 draws reagent from the appropriate reagent cartridge well in one of the Flex ™ M units 18 and then dispenses it into an assigned reaction vessel 17. The Flex ™ cartridges 18 each have a number of wells which contains the various reagents needed in either liquid or tablet form. The reagent arm 24 positions the reagent probe 26 to hydrate, mix and transfer reagents used in photometric tests. Stepping motors (not shown) rotate the arm and position the probe for aspiration and dispensing of reagents. The reagent probe 26 is an ultrasonic mechanism used for hydrating, aspirating, dispensing and mixing reagents. It can access reagent cartridges in one position and move the reaction vessels 17 at any of the active positions around the transport means 16. The hydration and mixing is all part of an existing commercial system and need not be described further.

As is known in the Dimension ® clinical chemistry system, cuvettes are formed by pulling two different composition ribbons of clear film from the cuvette film cartridge 30 onto the periphery of the transport means 16. The transport means, in the form of a cuvette wheel, has 100 separate cuvette cavities. The inner wall of each cavity has an inner wall to allow transmission of light. There is a cuvette forming station 32 in which an ionomer film ribbon is heat softened, molded onto the inner wall of the cuvette or reaction vessel cavity and its optical window. The transport means is then rotated to stretch the outer ionomer-nylon film ribbon across the molded inner film and the two are heat-bonded to each other. A small opening remains at the top of the cuvette to allow the addition of reagent and sample. A drive capstan 40 pulls the cuvette film moving the cuvettes clockwise about the cuvette wheel, i.e., the transport means 16.

After the cuvette is formed, the sample arm 14 draws a sample from a sample cup in the sample wheel 12 and adds it to the reaction vessel or cuvette 17. Sample mixing is performed ultrasonically by the sample probe. The reagent arm/probe 24/26 hydrates reagents automatically as they are needed. The reagent probe then adds hydrated reagent to the cuvette and ultrasonically mixes the sample and reagents together. A photometer 42 located beneath the reagent arm 24 and under the transport means 16 measures light absorbance through the cuvette at various wavelengths. A source lamp 44 emits a light beam which passes through various lens housed in a rotatable detector arm 45 to a photodetector 46 which, being mounted on the outer-end of the detector arm 45 adjacent the outer periphery of the cuvettes 17, rotates about the transport means 16. The photodetector relays absorbance readings through the computer where the readings are converted into concentration units.

Figure 4:
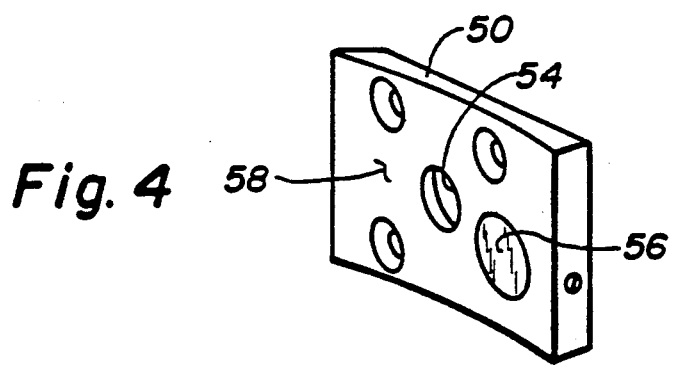
FIG. 4 is a pictorial representation of the magnet holder of FIG. 3.
Figure 5:
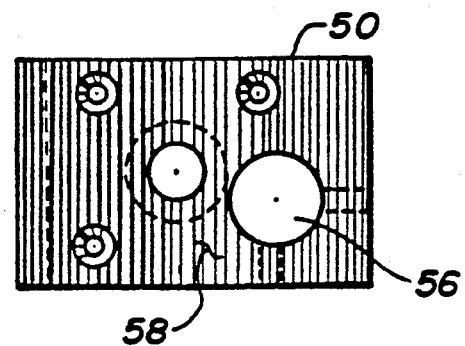
FIG. 5 is a front elevation view of the magnet holder of FIG. 4.

In accordance with this invention a magnet 56, positioned in a mounting block 50 (FIG. 4), is secured to the photodetector 46 whose inner face, facing the cuvettes, is best seen in FIG. 6. The inner face, or cover, of the photodetector of FIG. 6 has screw holes which conform to the screw hole locations in the mounting block 50. The access window for the photodetector 46 is illustrated at 48 (FIG. 6). The mounting block 50 is formed with an opening 54 to permit the passage of light through the holder. The block 50 positions a permanent magnet 56 to be spaced from the opening 54 a distance to correspond to the spacing between two adjacent cuvette positions. The magnet 56 is positioned such that the flux axis of the magnet cylinder will pass through approximately the bottom center of each cuvette such that the magnetic particles are withdrawn from the cuvette toward the bottom and sidewall thereof.

The magnet 56 is mounted in a position such that it has a flat circular surface 58 parallel to and approximately 2/32 inches removed from the wall of the cuvettes 17 which it is facing. The center of the magnet is at the same horizontal plane as mentioned at the bottom of the cuvette.

The permanent magnet 56 is cylindrical shaped, approximately 0.5 inch in diameter and 0.25 inches in height with a magnetic strength of approximately 2500 to 3000 gauss measured on the face of the magnet in a preferred embodiment. Other sizes, shapes, and strengths may be used.

In operation, the magnet is positioned, by its being mounted on the detector arm 45, one cuvette to the right of the optical axis of photometer 45 (cuvette +1), when the photometer arm 45 is instructed by program command to move to a selected cuvette position designated cuvette zero. Thus, with the solid phase magnetic particles being in "cuvette +1" position relation to the photometer arm, the magnet 56 pulls the particles out of suspension and against the side-bottom wall of the cuvette. This permits the reagent probe to "sip" the supernatant from the cuvette +1 position and transfer it to the cuvette zero position in a preferred embodiment, where it may be read by the photometer. The receptive cuvette may be any position on transport means 16, to where the reagent probe 26 and arm 24 are accessible. This is accomplished through the software of the computer 10.

Although the computer of the chemistry system may be programmed in any desired manner, one method by way of illustration for performing a digoxin assay may be described by the following pseudocode designations when used with the Dimension ® system: photometric method: "DIG"

| | |
|---|---|
| key = Oxe4 | |
| first cuvette: | {* pretreatment cuvette *} |
| −108.2 sec: | QC cuvette tag = "r1c1" |
| −94.0 sec: | add 80 µl of R1 {* first reagent [conjugate] *} |
| | followed by 20 µl of water |
| | ultra power = 0 |
| 0.0 sec: | add 80 µl of sample followed by 19 µl of water |
| | ultra power = 2 |
| | ultra ontime = 0.5 sec |
| | ultra duty cycle = 30% |
| | ultra cycle time = 105 msec |
| | ultra error rate = 40% |
| 240.0 sec: | add 80 µl of R2 {* second reagent [chrome] *} |
| | followed by 40 µl of water |
| | remix R2 at power level 7 for 5.0 sec |
| | ultra power = 8 |
| | ultra ontime = 0.5 sec |
| | ultra duty cycle = 50% |
| | ultra cycle time = 105 msec |
| | ultra error rate = 40% |
| 425.0 sec: | apply magnetic field for 20.0 sec | note:
{* sample rate *}
cuvette 2 time 0.0 lags that of cuvette 1 by 20.0 sec; 430.0 sec = = 450.0 sec of cuvette 1second cuvette:

| | |
|---|---|
| −125.0 sec: | QC cuvette tag = "r1" |
| 0.0 sec: | form cuvette {* in absence of sample delivery, we must explicitly ask for cuvette *] |
| 320.0 sec: | add 275 µl of R4 followed by 20 µl of |

-continued

| | |
|---|---|
| | water |
| | ultra power = 0 |
| 420.0 sec: | add 60 μl of first cuvette (height = 5.0 mm) followed by 30 μl of water |
| | ultra power = 8 |
| | ultra ontime = 0.5 sec |
| | ultra duty cycle = 50% |
| | ultra cycle time = 105 msec |
| | ultra error rate = 40% |
| 430.0 sec: | hardread cuvette tag = "rA" |
| 550.0 sec: | hardread cuvette tag = "rB" |
| calculation: | |
| float mauA = rA[405] − rA[510]; | |
| float mauB = rB[405] − rB[510]; | |
| legend[0] = "RDIG"; polished[0] = mauB − mauA; | |
| endcalc | | flex specification:

```
    |----R1----   |-----2-----   |----------|---R4--   |
/ 1   / 2    / 3   / 4    / 5   / 6   / 7   / 8  ||

|      |     |      |      |     |     |     |    ||
  |---conjugate---chrome--   |     | -----onpg----   ||
  |      |     |      |      |     |     |     |    ||
```

Interpretation

To simplify the interpretation, the times at which activities occur have been referenced with respect to the time of the first reagent delivery to the first cuvette. Activities which are grouped by cuvette in the specification are here placed in time order.

Those activities not relevant to the performance of the assay are not described.

The times appearing in square brackets can be used to back-reference to the assay specification.

0.0 sec [cuvette 1, −94.0 sec]
  Using the reagent probe, deliver 80 μL of conjugate reagent followed with 20 μL of water to the first cuvette.

94.0 sec [cuvette 1, 0.0 sec]
  Using the sample probe, deliver 80 μL of sample followed with 19 μL of water to the first cuvette. Mix the first cuvette using the ultrasonic mixing capability of the sample probe.

334.0 sec: [cuvette 1, 240.0 sec]
  Using the reagent probe, resuspend the particle reagent in the reagent container using the ultrasonic mixing capability of the reagent probe. Deliver 80 μL of this particle reagent followed by 40 μL of water to the first cuvette. Mix the first cuvette using the ultrasonic mixing capability of the reagent probe.

434.0 sec: [cuvette 2, 320.0 sec]
  Using the reagent probe, deliver 275 μL of ONDG reagent followed with 20 μL of water to the second cuvette.

519.0 sec: [cuvette 1, 425.0 sec]
  Using the photometer, sequester all particle in the first cuvette by placing the magnet affixed to the photometer arm next to the first cuvette. Remain at this position for 20.0 seconds.

534.0 sec: [cuvette 2, 420.0 sec]
  Using the reagent probe, aspirate 60 μL of supernatant from the first cuvette. Deliver this volume to the second cuvette, following immediately with 30 μL of water. Mix the second cuvette using the ultrasonic mixing capability of the reagent probe.

544.0 sec: [cuvette 2, 430.0 sec]
  Using the photometer, take an initial reading of the second cuvette.

664.0 sec: [cuvette 2, 550.0 sec]
  Using the photometer, take a final reading of the second cuvette.

An alternative embodiment of this invention is illustrated in FIG. 7 which depicts a bracket 70 that may be attached to the photometer arm 45 so as to extend along the outer periphery of the reaction vessels, i.e., cuvettes 17. Bracket 70 is in the form of an L and at one end of the bracket 70 is a magnet holder 72 which may be formed of a suitable engineering plastic or any there non-ferrous material. Three magnets 74, which may be the same as those used in connection with the embodiment described in connection with FIGS. 3 to 6, are positioned such that the inner surface 78 is flat and circular so as to be parallel to and 2/32 of an inch removed from the wall of the cuvettes 17 which it is facing. The magnets are positioned vertically such that the magnet is in the same horizontal plane as the bottom of the cuvette as previously described in connection with the embodiment of FIGS. 3 to 6.

The program commands are similar to those described in connection with the first embodiment of this invention and with this design the magnet is automatically positioned so that when the photometer arm 45 is instructed by a program command to move to any cuvette position, designed cuvette 0, the magnet is automatically positioned by the bracket 70 four (and sequentially thereafter when multiple magnets are used) cuvettes to the right of the photometer arm 45. Hence the magnets are positioned adjacent to cuvettes 4, 5 and 6. A magnetic test in positions 4, 5 or 6 could be interfered by any photometric measurements performed on cuvettes at positions 0, +1 or +2 at a time other than when magnetic separation is desired, because of the magnets in bracket 70. Hence cuvette positions 0, +1 and +2 are made unavailable for those non-magnetic test such that a premature magnetic separation on the magnetic test would never occur. With this embodiment using the bracket 70, a cuvette at a particular position may be subjected to the influence of a magnetic field for separation of the CPR through three cycles typically of 20 seconds each such that a full total of 1 minute would be used to separate the desired CPR. Other than that the operation is the same as that previously described.

Whichever embodiment is used, various heterogeneous assays may be performed without the use of pretreatment. Using these procedures, for example, on the Dimension ® clinical analyzer system: (a) Dispense ABC reagent (consists of anti-digoxin antibody to β-galactosidase conjugate) into cuvette A. (b) Dispense sample into cuvette A. Incubate for 1 to 5 minutes. (c) Dispense CPR (Oubain-BSA-coated $CrO_2$ particles). Incubate for 1 to 5 minutes. (d) Magnetic separation for 15-30 seconds. (e) Transfer an aliquot of supernatant to cuvette B, which contains o-nitrophenyl galactoside (ONPG) substrate solution. (f) Photometric measurement on cuvette B.

In short by providing a "smart" magnet module of this invention, which is software controllable, an automatic system is provided with a minimal of manual operations. In a preferred embodiment, the magnet is located one cuvette position (position +1) after the cuvette directly in line with the photometric detector (position 0) of the photometer arm 45. Recall, in the embodiment, and where the magnet is mounted on the cover of the photometric detector 46. This provides a system which is capable of performing heterogeneous immunoassays. The system is capable of operating with or without washing of the particles as part of the assay procedure. In addition to the conventional ACMIA assays, it is also able to perform enzyme immunoassays (EIA) employing either a sandwich or a competitive mode using magnetizable particles as a solid support. The EIA assays require washing of the solid support and sensitivities of $10^{12}$ mole/liter are obtained.

EXAMPLE 1

Enzymometric Immunoassay for Digoxin

Reagents:

The reagents described below are available commercially under the tradename DIG Flex ™ reagent cartridge (Part number 717035.901) which is intended for the detection of digoxin in human specimens using the Du Pont Dimension ® clinical chemistry system.

1. ANTIBODY-$\beta$-GALACTOSIDASE CONJUGATE REAGENT, hereafter designated Conjugate, is a covalently cross-linked aggregate of anti-digoxin antibody and $\beta$-galactosidase, formulated in a sodium biphosphate/sodium monophosphate buffer, pH 7.4. The Conjugate solution is contained in wells No. 1 and 2 of the Flex ™ reagent cartridge 18 (FIG. 2).

2. CHROMIUM DIOXIDE PARTICLE REAGENT, hereafter designated CPR, is a suspension of magnetizable chromium dioxide particles, on which a covalent coating of oubain-bovine serum albumin (Oubain-BSA) molecules has previously been introduced. Appropriate amount of CPR is formulated in a sodium biphosphate/sodium monophosphate buffer pH 7.4, and is contained in wells 3, and 4 of the Flex ™ reagent cartridge 18.

3. o-NITROPHENYL GALACTOSIDE REAGENT, hereafter designated ONPG, is a solution of o-nitrophenyl galactoside in a buffer consisting of N-2-hydroxyethylpiperazine-N'-2-ethanesulfonic acid (HEPES buffer), pH 7.8, and is contained in wells 7 and 8 of the Flex ™ reagent cartridge 18. ONPG is used as a colorimetric substrate for $\beta$-galactosidase. It is therefore feasible to substitute ONPG with another substrate for the enzyme and achieve similar results for the assay.

The following procedure can be used to perform a digoxin assay using the apparatus of this invention in the Dimension ® clinical chemistry system with the embodiment of FIG. 2.

Procedures

1. Prepare the Dimension ® clinical chemistry system per Operator's Guide (Part No. 715813.901) provided with the system.

2. Prior to testing specimens containing unknown concentration of digoxin, five calibrator samples are normally tested under the "Calibration" mode of the Dimension ® clinical chemistry system. The "assigned values" of each calibrator is manually entered into the computer before the tests. Load appropriate calibrators and a DIG Flex ™ reagent cartridge on the system. After the tests are completed, the on-board computer automatically performs a mathematical regression using the signals and assigned-values of all five samples. The regression employs an algorithm commonly known as "LOGIT function" and computes a series of "linearization coefficients". The coefficients are stored in the computer memory.

3. Schedule a digoxin test via the on-board computer. Load the specimen and a DIG FLEX ™ reagent cartridge containing the same lots of reagents as used in the Calibration step. The magnet-equipped Dimension ® clinical chemistry system performs the entire test automatically and uses the stored linearization coefficients to compute the concentration of digoxin by applying the LOGIT function in a reverse manner. The sequence of events by which the system performs the digoxin test follow.

4. Upon receiving commands to perform a digoxin test, the Dimension ® clinical chemistry system forms two cuvettes (A and B). The cuvettes, in a continuous chain-like formation, are situated around the perimeter of the Cuvette Wheel 16 (FIG. 2). The Cuvette Wheel is contained in a chamber which is maintained at a constant temperature of 37° C.

5. An aliquot of Conjugate (80 $\mu$L) is automatically withdrawn from the reagent cartridge and dispensed into Cuvette A by the system's Reagent Probe 26.

6. After 90 seconds, a sample of the specimen (80 $\mu$L) is withdrawn from the Sample Cup situated on Sample Wheel 12 and dispensed into Cuvette A by the system's Sample Probe 14. The Sample Probe is equipped with an ultrasonic device. After dispensing the specimen, the Probe is vibrated ultrasonically for 2 seconds while immersed in the solution. This provides agitation to allow thorough mixing of the specimen with the Conjugate solution.

7. After an incubation period of 180 to 360 seconds, an aliquot of CPR suspension (80 $\mu$L) is withdrawn from the reagent cartridge and dispensed into Cuvette A by the Reagent Probe. The Reagent Probe is also equipped with an ultrasonic device. Prior to withdrawing the CPR suspension from the reagent cartridge, the probe is vibrated ultrasonically for 5 seconds while immersed in the liquid to ensure consistent re-suspension of the CPR particles. After dispensing the suspension into Cuvette A, the probe is again vibrated for 2 seconds while immersed in the solution. This provides agitation to achieve consistent suspension of the CPR in the reaction mixture.

8. The mixture is allowed to incubate for approximately 2 minutes. During which the Conjugate molecules stoichiometrically bound to the digoxin molecules provided by the specimen remain in solution, while excess conjugate is bound by the Oubain-BSA coating on CPR particles.

9. While Cuvette A is incubating, an aliquot of ONPG (275 $\mu$L) is withdrawn from the reagent cartridge and dispensed into Cuvette B by the Reagent Probe.

10. Approximately 2 minutes after the dispensing of CPR, a command instructs the Photometer Arm 45 to move to a position, such that the permanent magnet is directly facing Cuvette A.

11. The Photometer Arm is held stationary for 20 seconds. This magnetizes the CPR and, in effect, holds the particles to the bottom and one side of the cuvette.

12. The Reagent Probe is commanded to withdraw a 60 $\mu$L aliquot of liquid, now free of CPR particles, from Cuvette A and dispense it into Cuvette B. While the Probe is immersed in Cuvette B, it is vibrated ultrasonically for 2 seconds. This step isolates the digoxin-bound Conjugate molecules, which is stoichiometrical to the unknown digoxin concentration, for enzymatic measurement in Cuvette B. Any and all excess Conjugate molecules are bound to the CPR and retained in Cuvette A.

13. After 10 seconds, the Photometer Arm is moved to allow the opening 54 of detector 46 (FIG. 3) to face Cuvette B. Absorbance at ten wavelengths are measured. The difference of absorbance between 405 nm and 510 nm are computed by the computer and recorded as rA (initial reading).

14. One hundred twenty (120) seconds after the initial reading, the Photometer is instructed to measure the absorbance of Cuvette B again. The difference of absorbance between 405 nm and 510 nm is computed and recorded as rB (second reading).

15. The difference between rB and rA is computed and recorded as the photometric signal of the test. The signal is used to compute the concentration of digoxin in the specimen as described in Step 3.

Results

TABLE 1

| Assigned Values | Digoxin Assay Calibration Results | | | | |
|---|---|---|---|---|---|
| | Signals (mA) | | Mean Signal | SD# | CV* |
| | Sample 1 | Sample 2 | | | |
| 0.00 ng/mL | 62.9 | 66.1 | 64.5 | 2.26 | 3.5% |
| 0.70 ng/mL | 82.8 | 81.4 | 82.1 | 0.99 | 1.2% |
| 1.20 ng/mL | 101.8 | 100.9 | 101.4 | 0.64 | 0.6% |
| 2.40 ng/mL | 114.8 | 116.5 | 115.7 | 1.20 | 1.0% |
| 5.00 ng/mL | 169.2 | 169.5 | 169.4 | 0.21 | 0.1% |

SD: Standard Deviation.
*CV: Coefficient of Variance. It is calculated by dividing SD with Mean.

Using this procedure, tests were run on digoxin samples with the following results:

Table 1 exhibits a set of results obtained from five calibrators. The "Assigned Values" (in ng/mL) and the mean signal (in mili-absorbance unit, mA) are used by the on-board computer to perform a regression analysis by the LOGIT function.

Table 2 shows testing results of ten serum specimens. The results, in ng/mL of digoxin concentration, are calculated by the computer automatically. The data indicates that the test results are in close agreement with those obtained by the Stratus TM system.

TABLE 2

| | Digoxin Test Results in Comparison to Results by A Commercial Test (Stratus) | |
|---|---|---|
| Serum No. | Dimension ® System | Stratus* System |
| 1 | 0.93 ng/mL | 0.90 ng/mL |
| 2 | 1.21 | 1.20 |
| 3 | 1.92 | 2.00 |
| 4 | 1.17 | 1.10 |
| 5 | 0.89 | 0.90 |
| 6 | 1.23 | 1.20 |
| 7 | 0.77 | 0.60 |
| 8 | 0.95 | 0.80 |
| 9 | 1.15 | 1.40 |
| 10 | 1.39 | 1.20 |

*Stratus TM Immunoassay System, manufactured by Baxter Healthcare Co., Dade Division, Miami, FL 33152

EXAMPLE 2

Procedure for Enzymometric Assay for Vitamin B12

Reagents
I. Releasing reagents

These reagents are provided in glass vials. Their function is to treat the serum specimen in such a way that the vitamin B12 molecules contained therein are released and available for the enzymometric detection.

1. DENATURING REAGENTS: Two reagents, a 0.1N sodium hydroxide (NaOH) solution and a 20 mM dithiothriotol (DTE) solution, are provided in separate vials.

2. NEUTRALIZING REAGENT: A sodium phosphate/N-2-hydroxyethylpiperazine-N'-2-ethanesulfonic acid (Phosphate/HEPES) buffer, pH 5.0.

II. Reagents provided by Flex TM reagent cartridge

The reagents described below are presented to the Dimension ® clinical chemistry system in a B12 Flex TM reagent cartridge. Either embodiment of the invention can be used.

1. INTRINSIC FACTOR TO β-GALACTOSIDASE CONJUGATE REAGENT, hereafter designed IFC, is a covalently cross-linked aggregate of β-galactosidase and calf intestinal intrinsic factor. Intrinsic factor is a protein which possesses high affinity to vitamin B12 and whose natural function is to transport vitamin B12 molecules through the biological systems. A highly purified form of this protein is used in this assay to detect vitamin B12 in human serum with high sensitivity and specificity. The IFC is formulated in a sodium biphosphate/sodium monophosphate buffer, pH 7.8 and is contained in wells 1 and 2 of the B12 Flex TM reagent cartridge 18 (FIG. 2).

2. VITAMIN B12-COATED CHROMIUM DIOXIDE PARTICLE REAGENT, hereafter designated B12-CPR, is a suspension of chromium dioxide particles which have been covalently coated with a layer of a vitamin B12-avidin conjugate. The reagent is formulated in a sodium biphosphate/sodium monophosphate buffer, pH 7.4. Appropriate amount of B12-CPR suspension is contained in Wells 3 and 4 of the B12 Flex TM reagent cartridge 18.

3. CHLOROPHENOL RED-β-D-GALACTOPYRANOSIDE REAGENT, hereafter designated CPRG, is a solution of chlorophenol red-β-D-galactopyranoside in a buffer consisting of N-2-hydroxyethylpiperazine-N'-2-ethanesulfonic acid (HEPES buffer) pH 7.8, and is contained in wells 7 and 8 of the Flex TM reagent cartridge 18. CPRG is used as a colorimetric substrate for β-galactosidase.

Procedure

1. Prepare the Dimension ® clinical chemistry system according to procedures specified in the Operator's Guide.

2. In a plastic or glass test tube, sequentially dispense 200 μL of serum specimen or calibrator, 20 μL of NaOH solution and 20 μL of DTE solution. Allow the mixture to stand at ambient temperature for 5 minutes. This step brings the pH of the specimen to higher than 12, which denatures most or all the serum proteins, including endogenous intrinsic factor, such that any and all vitamin B12 molecules are released into the solution. The DTE reagent helps to block the sulfohydryl groups on the denatured proteins, therefore preventing any re-capturing of the vitamin B12 molecules.

3. Dispense 60 μL of the neutralizing reagent into the test tube. Vortex to mix the solutions. The pH is reduced to 7.4 to 7.8 at this stage. This step readies the specimen for the subsequent enzymometric test.

4. Prior to testing specimens containing unknown concentration of vitamin B12, five calibrator samples are tested under the "Calibration" mode of the Dimension ® clinical chemistry system. The "assigned values" of each calibrator is manually entered into the computer before the tests. Load appropriate calibrators and a B12 Flex TM reagent cartridge on the system. After the tests are completed, the computer calculates and stores a set of linearization coefficients much like described in Example 1.

5. Schedule a vitamin B12 test via the on-board computer. Load the specimen processed in steps 2 to 3 and a B12 Flex TM reagent cartridge containing the same lots of reagents as used in the Calibration step. The magnet-equipped Dimension ® clinical chemistry system performs the entire test automatically and uses the stored linearization coefficients to compute the concentration of vitamin B12 by applying the LOGIT function in a reverse manner. The sequence or events by which the system performs the vitamin B12 test follow.

6. The Dimension ® clinical chemistry system forms two cuvettes (A and B). The entire cuvette wheel is contained in a chamber which is maintained at approximately 37° C.

7. An aliquot of IFC (100 µL) is automatically withdrawn from the reagent cartridge and dispensed into Cuvette A by the system's Reagent Probe.

8. After 90 seconds, a sample of the specimen (50 L) is withdrawn from the Sample Cup and dispensed into Cuvette A by the system's Sample Probe. The Probe is vibrated ultrasonically for 2 seconds.

9. After an incubation period of 180 to 360 seconds, an aliquot of B12-CPR suspension (80 µL) is withdrawn from the reagent cartridge and dispensed into Cuvette A by the Reagent Probe. The Probe is ultrasonically vibrated for 5 seconds while immersed in the B12-CPR suspension in reagent cartridge 18 and vibrated for 2 seconds after dispensing the suspension into cuvette 17.

10. The mixture is allowed to incubate for approximately 2 minutes.

11. While Cuvette A is incubated, an aliquot of CPRG (275 µL) is withdrawn from the reagent cartridge and dispensed into Cuvette B by the Reagent Probe.

12. Approximately 2 minutes after the dispensing of B12-CPR, the Photometer Arm is moved to allow the permanent magnet to act on Cuvette A directly.

13. The Photometer Arm is held stationary for 20 seconds. The magnetized B12-CPR particles are held to the bottom and one side of the cuvette.

14. The Reagent Probe withdraws a 50 µL aliquot of the supernatant, now free of B12-CPR particles, from Cuvette A and dispenses it into Cuvette B. After dispensing the liquid, the probe is vibrated ultrasonically for 2 seconds.

15. Absorbance measurement on Cuvette B is taken both at 10-second and 100-second after the completion of step 14. The difference of absorbance between 577 nm and 700 nm of both measurements is computed. The results for each measurements are recorded as rA and rB, respectively.

16. The difference between rB and rA is computed and recorded as the photometric signal. The signal is used to compute the concentration of vitamin B12 using the stored linearization coefficients by applying the LOGIT function in a reverse manner.

Results

TABLE 3

| Vitamin B12 Assay Calibration Results | | | | |
|---|---|---|---|---|
| Assigned | Signals (mA) | | Mean | | |
| Values | Sample 1 | Sample 2 | Signal | SD# | CV* |
| 0. pg/mL | 697 | 772 | 734 | 53.0 | 7.2% |
| 25 pg/mL | 823 | 842 | 833 | 13.0 | 1.6% |
| 100 pg/mL | 851 | 849 | 850 | 1.3 | 0.2% |
| 400 pg/mL | 890 | 889 | 890 | 0.4 | 0.05% |
| 1,000 pg/mL | 937 | 1007 | 972 | 49.0 | 5.1% |

SD: Standard Deviation.
*CV: Coefficient of Variance. It is calculated by dividing SD with Mean.

Table 3 exhibits the results of vitamin B12 calibrators tested by the procedures described above. The 400 pg/mL calibrator was diluted with equal volume of the 0 pg/mL calibrator and tested by the system. The sample has a theoretical vitamin B12 concentration of 200 pg/mL. The Dimension ® system produced a result of 220 pg/mL. This result is sufficiently close to the theoretical value to be clinically useful.

EXAMPLE 3

Enzymeimmunoassays

It is conceivable that the Dimension(r) system equipped with the magnet module of the invention can be used to perform another type of heterogeneous immunoassay, commonly known as Enzyme Immunoassay (EIA). The modified system can perform at least two types of EIA, sandwich immunoassay and competitive immunoassay, by employing appropriate program commands. The sequence of events required for these two types of tests is described as follow.

SANDWICH IMMUNOASSAYS: In this type of tests, magnetizable chromium dioxide particles ($CrO_2$) are used as solid support, on which an antibody (Capturing Ab) to an analyte of interest is covalently coated. An aliquot of the suspension of $CrO_2$ and a specimen, in which the analyte of interest resides, are dispensed into a cuvette (Cuvette A) of the Dimension ® system in close succession. Either immediately afterward or following an incubation period, a solution containing an Detector Antibody-enzyme conjugate is dispensed into the same cuvette. Following a second incubation period, the magnet is moved next to Cuvette A, achieving magnetic separation of $CrO_2$ from the liquid. The Reagent Probe is commanded to withdraw the entire liquid content from the cuvette.

Thereafter, a cleaning solution, consisting of either water or an appropriate buffer, is dispensed into Cuvette A. The Probe is ultrasonically vibrated for a preprogrammed period to enhance mixing of the particles in the cleaning solution. The magnet is held next to the cuvette, such that as soon as the ultrasonic vibration subsides, the particles are attracted to one side and away from the liquid. The Particle Washing routine, which consists of removal of contaminated liquid, dispensing of fresh cleaning solution, ultrasonic mix and $CrO_2$ separation is performed twice thereafter.

These steps, conceivably performed automatically by the Dimension ® system, results in a $CrO_2$-bound "sandwich" which consists of, in sequence, the Capturing Ab, the analyte of interest and the Detector Antibody-enzyme conjugate. The solid-phase bound sandwich conglomerate is substantially free of contaminating serum components and excessive Detector Antibody-enzyme conjugate molecules due to the trice washing procedure.

Upon completing the Particle Washing routine, the magnet is moved away from Cuvette A. A solution containing an appropriate substrate of the enzyme is dispensed onto the $CrO_2$ particles, now substantially free of liquid. The Reagent Probe is vibrated ultrasonically to achieve mixing of the particles. The enzyme molecules on the solid-phase bound sandwich is allowed to react with the substrate for a pre-programmed period of time. During the reaction period, a quench solution, which is capable of stopping the enzyme reaction, is dispensed into a second cuvette (cuvette B), which commonly follows Cuvette A. Upon completion of the enzyme-to-substrate reaction, the magnet is moved next to Cuvette A which again separates the $CrO_2$ from the liquid. The Reagent Probe withdraws a portion of the liquid from Cuvette A and dispenses it into Cuvette B. Upon mixing with the quench solution, any residual enzymatic reaction is stopped. Two photometric measurements are taken on Cuvette B, one before and one after the liquid transfer. The difference between the two measurements, which is stoichiometric to the concentration of the analyte, is computed and recorded as signal.

Similar to the Calibration procedure described in Example 1, a set of calibrators with known concentration of the analyte is tested before any unknown specimen. The signals resulted from the testing of the calibrators are computed by a regression function to derive a set of regression coefficients. These coefficients are stored in the computer memory and used for computing the concentration of the analyte of an unknown specimen tested subsequently.

COMPETITIVE IMMUNOASSAYS: This type of test deviates from the Sandwich Immunoassay in that a purified form of the analyte or its chemical derivative is covalently coated on the solid support, the chromium dioxide particles ($Ag-CrO_2$).

An aliquot of $Ag-CrO_2$ suspension, a specimen containing the analyte of interest and a Detector Antibody-enzyme conjugate solution are dispensed into Cuvette A in a similar fashion as those described in the Sandwich Immunoassays. Similar incubation periods are allowed.

The particle washing routine, as described in the Sandwich Immunoassays, is employed to clean the particles three times. In this type of test, the $CrO_2$-bound analyte molecules compete against the analyte molecules provided by the specimen for the binding sites on the Detector-Antibody molecules. The competitive reaction results in a linkage of $CrO_2$-bound analyte to the Detector Antibody-enzyme conjugate. The concentration of such linkage is inversely related to the concentration of the analyte in the specimen.

The substrate solution dispensing, ultrasonic mixing, incubation in Cuvette A are all performed in a manner similar to the Sandwich Immunoassays. Subsequent dispensing of quench solution into Cuvette B, magnetic separation in Cuvette A, liquid transfer, photometric measurements and computation of the test results are all processed in a fashion similar to the Sandwich immunoassays.

What is claimed is:

1. An automatic apparatus for use in assays for separating magnetic particles from a liquid phase, the apparatus comprising:
    a plurality of reaction vessels for holding magnetic particles dispersed in a liquid phase,
    a reaction vessel mounting wheel for moving the plurality of reaction vessels in sequence past at least one processing position,
    probe means for dispensing liquid into and withdrawing liquid from the plurality of reaction vessels,
    a reaction monitoring arm mounted for relative movement with respect to the reaction vessel mounting wheel and to be positioned with its periphery adjacent any of the plurality of reaction vessels,
    a detector positioned on the reaction monitoring arm radially outside of the plurality reaction vessels, the reaction monitoring arm being operable to direct a beam of interrogating radiation through each plurality of reaction vessles to the detector, and
    coupling means coupled to the reaction monitoring arm for selectively positioning a first magnet adjacent the location of the beam of interrogating radiation, but spaced therefrom by the distance separating adjacent plurality of reaction vessels on the reaction vessel mounting wheel.

2. The automatic apparatus of claim 1 wherein a magnet is mounted on the detector radially outside of the plurality of reaction vessels.

3. The automatic apparatus of claim 1 which includes second and third magnets; and wherein the coupling means positions the second and third magnets adjacent the first magnet, whereby the plurality of reaction vessels are sequentially positioned and are simultaneously subjected to a magnetic field.

4. The automatic apparatus of claim 3 wherein the coupling means is a bracket secured to the periphery of the reaction monitoring arm.

5. The automatic apparatus of claim 3 wherein the probe means is operable to transfer liquid in a vessel subjected to any magnet to another vessel free of the magnetic particles.

* * * * *